US00PP34013P2

(12) United States Plant Patent
Lim

(10) Patent No.: US PP34,013 P2
(45) Date of Patent: Mar. 15, 2022

(54) ***HIBISCUS* PLANT NAMED 'ALTYELLOWRIVER'**

(50) Latin Name: *Hibiscus rosa-sinensis*
Varietal Denomination: ALTYELLOWRIVER

(71) Applicant: Altman Specialty Plants, Inc, Vista, CA (US)

(72) Inventor: Peter Lim, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/356,884

(22) Filed: Jun. 24, 2021

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ... A01H 5/02; A01H 5/00; A01H 6/60; A01H 6/608
See application file for complete search history.

(56) References Cited

PUBLICATIONS

*Hibiscus* Lady, retrieved on Aug. 30, 2021, retrieved from the Internet at https://www.hibiscusladyhawaii.com/copy-of-strawberry-champagne, one page. (Year: 2021).*
Hidden Valley Nature Arts, retrieved on Aug. 30, 2021, retrieved from the Internet at https://www.hiddenvalleynaturearts.com/acatalog/daisymae.htm, 5 pp. (Year: 2021).*

* cited by examiner

*Primary Examiner* — June Hwu
(74) *Attorney, Agent, or Firm* — Cassandra Bright

(57) ABSTRACT

A new and distinct cultivar of *Hibiscus* plant named 'ALTYELLOWRIVER' is disclosed, characterized by rich yellow flowers with dark red centers, thick petals, and dark, dense, glossy foliage that is resistant to leaf spot disease. Plants are dwarf and bushy, with a high flower count. The new variety is a *Hibiscus*, typically produced as an ornamental plant.

1 Drawing Sheet

Latin name of the genus and species: *Hibiscus rosa-sinensis*.

Variety denomination: 'ALTYELLOWRIVER'.

BACKGROUND OF THE INVENTION

The new *Hibiscus* cultivar is a product of a planned breeding program conducted by the inventor, Peter Lim. The objective of the breeding program was to produce vigorous *Hibiscus rosa-sinensis* cultivars with healthy foliage. The cross resulting in this new variety was made Jun. 10, 2012.

The seed parent is the unpatented *Hibiscus rosa-sinensis* 'Luau Lilikoi Yellow'. The pollen parent is the unpatented variety *Hibiscus rosa-sinensis* 'Daisy Mae'. The new variety was identified and selected as a potentially interesting selection in September of 2014. Selection was made at a commercial nursery in Vista, Calif.

Asexual reproduction of the new cultivar 'ALTYELLOWRIVER' was first performed in September 2014 in Vista, Calif., by vegetative cuttings. Subsequent propagation has shown that the unique features of this cultivar are stable and reproduced true to type in successive generations.

SUMMARY OF THE INVENTION

The cultivar 'ALTYELLOWRIVER' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTYELLOWRIVER'. These characteristics in combination distinguish 'ALTYELLOWRIVER' as a new and distinct *Hibiscus* cultivar:

1. Rich yellow flowers with dark red ring in center.
2. High flower count.
3. Dwarf, bushy plant.
4. Resistant to leaf spot disease.
5. Dark, dense, glossy foliage.

PARENT COMPARISONS

Plants of the new cultivar 'ALTYELLOWRIVER' are similar to the seed parent 'Luau Lilikoi Yellow', in most horticultural characteristics. However, characteristics of the new cultivar differ in the following:

1. The new variety has a higher flower count per plant than that of the seed parent.

Plants of the new cultivar 'ALTYELLOWRIVER' are similar to the pollen parent 'Daisy Mae', in most horticultural characteristics. However, characteristics of the new cultivar differ in the following:

1. The new variety has a higher flower count per plant than that of the pollen parent.
2. Plants of the parent variety are approximately 50% to 100% larger at maturity than the new variety.

3. Flowers of the new variety are approximately 12 to 13 cm in diameter on average, flowers of the parent variety are approximately 18 cm in diameter on average.

COMMERCIAL COMPARISON

Plants of 'ALTYELLOWRIVER' are similar in some horticultural characteristics to the variety *Hibiscus* 'Lemon Drop Kid', unpatented. The new variety, however, differs in the following:

1. Flowers of 'ALTYELLOWRIVER' are smaller than flowers of 'Lemon Drop Kid'.
2. Plants of 'Lemon Drop Kid' have a taller plant habit than 'ALTYELLOWRIVER'.
3. Flowers of 'ALTYELLOWRIVER' are yellow with dark red eye, while flowers of 'Lemon Drop Kid' are lemon-yellow with a red eye.

Plants of 'ALTYELLOWRIVER' are similar in some horticultural characteristics to the variety *Hibiscus* 'Lemon Lollipop', unpatented. The new variety, however, differs in the following:

1. Flowers of 'ALTYELLOWRIVER' are smaller than flowers of 'Lemon Lollipop'.
2. Plants of 'Lemon Lollipop' have a taller growth habit than 'ALTYELLOWRIVER'.
3. Flowers of 'ALTYELLOWRIVER' are yellow with dark red eye, while flowers of 'Lemon Lollipop' are yellow with a cherry-red eye.

BRIEF DESCRIPTION OF THE PHOTOGRAPH

The accompanying photograph illustrates in full color a typical flower of 'ALTYELLOWRIVER' from a plant grown outdoors at a commercial nursery in Vista, Calif. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a 'ALTYELLOWRIVER' plant. This plant was grown at a commercial nursery in Vista, Calif. The growing temperature ranged from about 7° C. to 30° C. during the day and from about 5° C. to 12° C. during the night. No artificial light, photoperiodic treatments were given to the plants. Measurements and numerical values represent averages of typical plant types.

Botanical classification: *Hibiscus rosa-sinensis* 'ALTYELLOWRIVER'.

PROPAGATION

Typical method: Hardwood stem cuttings.

Root description: Roots are fine, fibrous and well branched. Tan/brown in color, not effectively measured with a color chart.

PLANT

Plant type: Tender, woody flowering shrub.

Age of plant described: Approximately 2 years old.

Growth habit: Compact.

Height: 90 cm.

Plant spread: 70 cm.

Branching characteristics: 2 to 4 breaks from a pinch, occurring at an average 45° angle.

Length of primary lateral branches: 20 to 60 cm.

Quantity of lateral branches: About 12 to 18.

Characteristics of primary lateral branches:

*Diameter.*—Average range 10 to 14 mm.

*Color.*—New growth near RHS Green 144B, mature growth near RHS Greyed-Green 197D, infrequently striated Grey-Brown 199C.

*Texture.*—New growth very slightly hirsute, older growth slightly striated.

Internode length: Average 3 cm.

FOLIAGE

Leaf:

*Arrangement.*—Alternate.

*Quantity.*—Average 12 to 16 per branch.

*Average length.*—10 cm, including petiole.

*Average width.*—9.5 cm.

*Shape of blade.*—Obovate to orbicular.

*Apex.*—Acute.

*Base.*—Obtuse.

*Margin.*—Crenate.

*Texture of top surface.*—Glabrous.

*Texture of bottom surface.*—Glabrous.

*Color.*—Young foliage upper side: RHS Green 139A. Young foliage under side: RHS Green 137A. Mature foliage upper side: RHS Green 137A. Mature foliage under side: RHS Green 137C.

*Venation.*—Type: Pinnate. Venation color, upper side: RHS Green 138B. Venation color, under side: RHS Yellow-Green 144A.

*Petiole.*—Length: 5 to 5.5 cm. Diameter: 3 to 4 mm. Color: Near RHS Yellow-Green 146A, base lightly flushed Greyed-Purple N186A. Texture: Densely short hirsute.

*Leaf stipule.*—Not observed.

FLOWER

Natural flowering season: Late Spring through Summer.

Flower type and habit: Solitary, rotate.

*Single, double, multiplex.*—Single.

*Petals overlapping.*—Moderately overlapping.

Quantity of flowers: A plant of about 2 years old has approximately 20 to 30 open flowers at one time during Summer.

Rate of flower opening: 5 to 8 days from bud to fully opened flower.

Flower longevity on plant: 1 to 2 days.

Persistent or self-cleaning: Self-cleaning.

Bud:

*Shape.*—Ovate.

*Length.*—4.5 cm.

*Diameter.*—2.1 cm.

*Color.*—RHS Yellow-Green 151D, lightly flushed Green 138B.

Flower size:

*Diameter.*—12.8 cm.

*Depth.*—8 cm.

Petals:
*Quantity.*—5.
*Arrangement.*—Whorled, moderately overlapping.
*Length.*—8.5 cm.
*Width.*—6.5 cm.
*Shape.*—Asymmetrical broad spatulate.
*Apex.*—Obtuse rounded with very slight, shallow crenations, slightly rolled upward with age.
*Base.*—Attenuate.
*Margin.*—Entire. Weak undulation.
*Texture.*—Glabrous all surfaces; underside rugose.
*Color.*—When opening, upper surface: RHS Yellow 12A, basal blotch (forming flower eye) Red 46A. When opening, lower surface: RHS Yellow 13B, basal area Yellow 13D. Fully opened, upper surface: RHS Yellow 13B. Basal blotch (forming flower eye) Red 46B with uppermost edge/halo White 155B. Fully opened, lower surface: RHS Yellow 13C, basal area Yellow 13D flushed Purple N77C. Ratio of basal blotch/eye to petal size: About 10% to 20% of petal blade blotched. Feathering: No feathering. Blotched eye with halo.

Sepals:
*Quantity.*—5.
*Length.*—2.5 cm.
*Width.*—1.2 cm.
*Shape.*—Ovate.
*Margin.*—Entire.
*Apex.*—Acute.
*Base.*—Fused.
*Color.*—Upper surface: RHS Green 138B. Lower surface: RHS Yellow-Green 144A.
*Texture.*—Upper surface: Softly pubescent. Lower surface: Very short hirsute.

Epicalyx:
*Quantity of bracts.*—5.
*Bract length.*—1.7 cm to 2.2 cm.
*Bract width.*—3 to 6 mm.
*Bract shape.*—Narrow deltate.
*Bract margin.*—Entire.
*Color.*—Upper surface: RHS Green 137B. Lower surface: Near RHS Green 137A.
*Texture.*—Glabrous all surfaces.

Peduncles:
*Length.*—4.5 to 5.5 cm.
*Diameter.*—4 to 5 mm.
*Angle.*—Approximately 45° to the lateral branch.
*Strength.*—Strong.
*Texture.*—Roughly pubescent.
*Color.*—RHS Yellow-Green 144A.

Fragrance: Faint musty scent.

REPRODUCTIVE ORGANS

Stamens:
*Number.*—About 60 to 80.
*Filament length.*—5 to 7 mm.
*Filament color.*—Near RHS White 155D.

Anthers:
*Shape.*—Irregular sphere.
*Length.*—About 2 mm.
*Color.*—Near RHS Yellow-Orange 22A.
*Pollen color.*—Near RHS Yellow-Orange 22A.
*Pollen amount.*—Scant.

Pistil:
*Number.*—1.
*Length.*—9.5 cm.
*Style.*—Length: 7.2 cm. Color: Lower section near Red 45B, mid-section near Yellow 10C. Highly iridescent throughout.
*Stigma.*—Shape: Peltate. Color: Near RHS Orange N25B.
*Ovary color.*—Near RHS Yellow 9C.

OTHER CHARACTERISTICS

Seeds: Not observed.

Disease/pest resistance: Observed resistance to leaf spot disease (assumed *Pseudomonas syringae*). No other resistance nor susceptibility to normal diseases and pests of *Hibiscus rosa-sinensis* have been observed.

Temperature tolerance: USDA Zones 8 through 11.

What is claimed is:

1. A new and distinct cultivar of *Hibiscus* plant named 'ALTYELLOWRIVER' as herein illustrated and described.

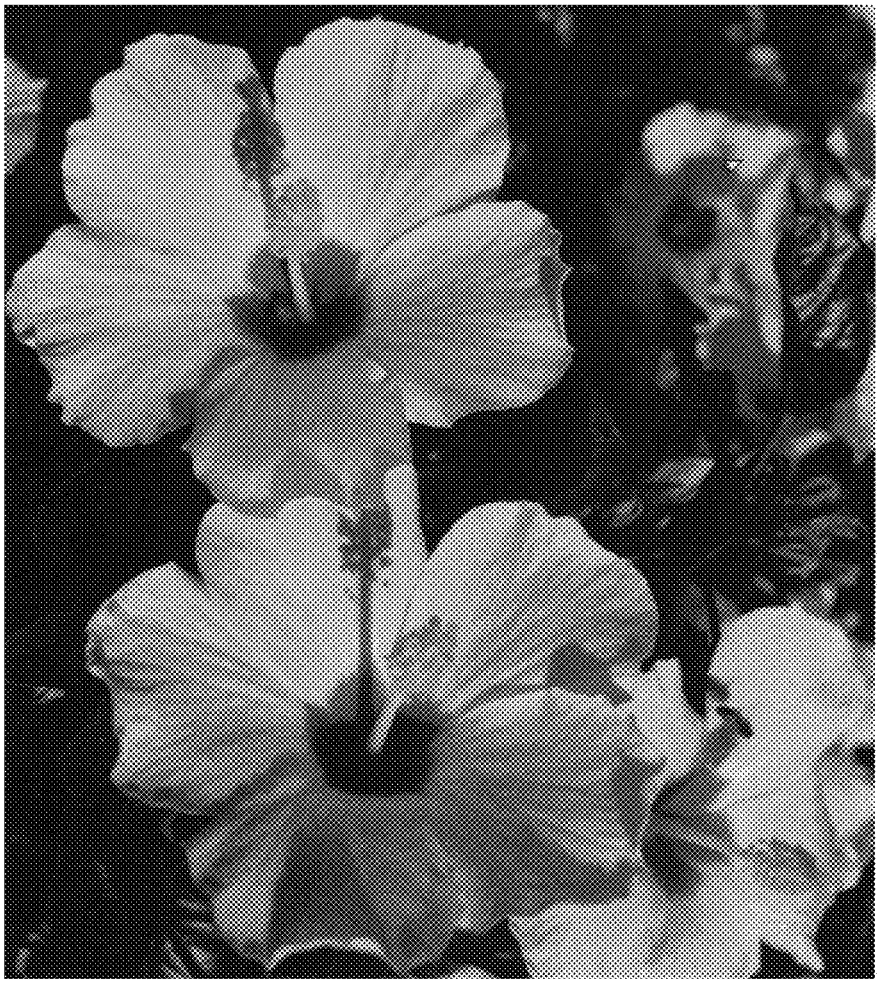

* * * * *